United States Patent [19]
Gammer et al.

[11] Patent Number: 5,549,712
[45] Date of Patent: Aug. 27, 1996

[54] FOREARM LIFTER

[75] Inventors: Peter Gammer; Heinz Broeckl; Hans Dietl, all of Vienna, Austria

[73] Assignee: Otto Bock Orthopaedische Industrie Besitz- und Verwaltungs-Kommanditgesellschaft, Duderstadt, Germany

[21] Appl. No.: 272,036

[22] Filed: Jul. 8, 1994

[30] Foreign Application Priority Data

Jul. 21, 1993 [DE] Germany ............... 43 24 399.1

[51] Int. Cl.⁶ ........................................... A61F 2/58
[52] U.S. Cl. ............................. 623/60; 623/57; 623/59
[58] Field of Search .................... 623/57, 59, 60; 482/99, 100, 101, 102, 120; 901/12, 15, 26, 28

[56] References Cited

U.S. PATENT DOCUMENTS

| | | |
|---|---|---|
| 1,644,833 | 2/1927 | Hoare ............................ 623/60 |
| 2,516,791 | 7/1950 | Motis et al. .................... 623/59 |
| 2,537,402 | 1/1951 | Fitch . | 
| 2,553,830 | 5/1951 | Motis . |
| 2,592,842 | 4/1952 | Alderson ....................... 623/60 |
| 2,626,398 | 1/1953 | Grindle et al. . |
| 3,107,358 | 10/1963 | Prout . |
| 4,604,098 | 8/1986 | Seamone et al. ................ 623/60 |
| 4,957,281 | 9/1990 | Christolear, Jr. ............... 482/100 |
| 5,104,121 | 4/1992 | Webb ............................ 482/100 |

FOREIGN PATENT DOCUMENTS 2751192  6/1978  Germany .

*Primary Examiner*—David H. Willse
*Assistant Examiner*—Bruce E. Snow
*Attorney, Agent, or Firm*—Foley & Lardner

[57] ABSTRACT

A forearm lifter for assisting in the articulation of a mating forearm part of an arm prosthesis with respect to a mating upper arm part about at least one elbow axis is disclosed. The forearm lifter includes: (i) a spring element; (ii) a mechanism having an input and an output, with the spring element directly or indirectly applying a tensile force to the input of the mechanism; and (iii) a tension element having one end acted upon by the output of the mechanism, and having another end which can be fastened at a fixed point on said mating upper arm part. The fixed point and the elbow axis define a torque lever, such that the force that is transmitted through the mechanism from the spring element applies torque to the mating upper arm part in such a manner that the curve of the torque acting at the fixed point, plotted against the angle of articulation of said forearm part, is approximately parabolic. The torque has its minimum values in both the forearm extended position and at maximum forearm bending. The torque has its maximum value when said upper arm mating part and said forearm are at approximately 90°.

20 Claims, 5 Drawing Sheets

FOREARM LIFTER

BACKGROUND OF THE INVENTION

1. Field of the Invention

The invention relates to a method of applying a torque to the upper arm of an arm prosthesis in order to swivel the forearm with the aid of a spring force.

The invention furthermore relates to a forearm lifter for an arm prosthesis in which the upper arm is articulately connected by means of at least one elbow axis to the forearm, the swiveling of which is assisted by a spring element.

2. Description of Related Art

In the construction of prostheses, a distinction is made between active and passive prostheses. This distinction is made in accordance with the performance capacity of the prosthesis. Those which are controlled by their own force or by an external force belong to the group of active prostheses. Among the prostheses utilizing their own force, the arm prosthesis equipped with power traction occupies an outstanding place. The arm, together with the gripping element or hand, is predominantly subjected to tensile stress through the force of gravity. Design solutions are therefore sought to relieve them of tensile stress. In the active arm prosthesis the voluntary bending of the forearm is initiated through Bowden cables by means of shoulder bandages of elastic material. This is done by shortening the bending cable, the fastening between the upper arm and the forearm being made at one end of the cable, while the force is transmitted via the shoulder to the upper arm of the other cable.

These prosthesis systems have the disadvantage of the prosthesis wearer becoming tired because there is no compensation for the weight of the forearm. In addition, optimum use cannot be made of the range of the bending function of the prosthesis. Various technical solutions have been developed for the purpose of compensating for the weight of the forearm. The designs most commonly used are spring assistance systems applied near the articulation point. Among the disadvantages of these designs is that the highest torque to assist the bending movement is applied in the extended position of the forearm, and this torque is reduced on the bending of the forearm. The torque curve is therefore exactly the opposite of the actual requirements. Another disadvantage of these previously known solutions is the fact that excessive increases of the torque hinders the free swinging phase, and thus the natural appearance in the pendulum phase of the forearm is disturbed.

SUMMARY OF THE INVENTION

One of the objects of the present invention is to develop a forearm lifter device and method which solves the problems of the known art discussed above.

Another object of the present invention is to provide an arm prosthesis which includes the forearm lifter of the present invention.

In accomplishing the foregoing objectives, there has been provided according to one aspect of the present invention, a forearm lifter for assisting in the articulation (swivelling) of a mating forearm part of an arm prosthesis with respect to a mating upper arm part about at least one elbow axis. The forearm lifter includes: (i) a spring element; (ii) a mechanism having an input and an output, with the spring element directly or indirectly applying a tensile force to the input of the mechanism; (iii) a tension element having one end acted upon by the output of the mechanism, and having another end which can be fastened at a fixed point on said mating upper arm part, and wherein the fixed point and the elbow axis define a torque lever, such that the force that is transmitted through the mechanism from the spring element applies torque to the mating upper arm part in such a manner that the curve of the torque acting at the fixed point, plotted against the angle of articulation of the mating forearm part, is approximately parabolic, and the torque has its minimum values in both the forearm extended position and at maximum forearm bending, and the torque has its maximum value when said upper arm mating part and the mating forearm part are at approximately 90°.

The present invention also provides a method of applying torque to the upper arm part of an arm prothesis. The method includes the step of articulating (swivelling) a mating forearm part with the aid of a spring force in such a manner that when the torque curve is plotted against the angle of bend of the mating forearm part with respect to the upper arm it is approximately parabolic and has its minimum values when the forearm part is extended and at maximum forearm bending, and has its maximum value when the angle of bend is approximately 90°.

The present invention also provides, a combination arm prothesis. The combination arm prosthesis includes the forearm lifter, a mating upper arm part, and a mating forearm part.

Further objects, features and advantages of the present invention will become apparent to persons skill in the art from the detailed description of preferred embodiments that follows.

DETAILED DESCRIPTION OF THE PREFERRED EMBODIMENTS

Figure 1:
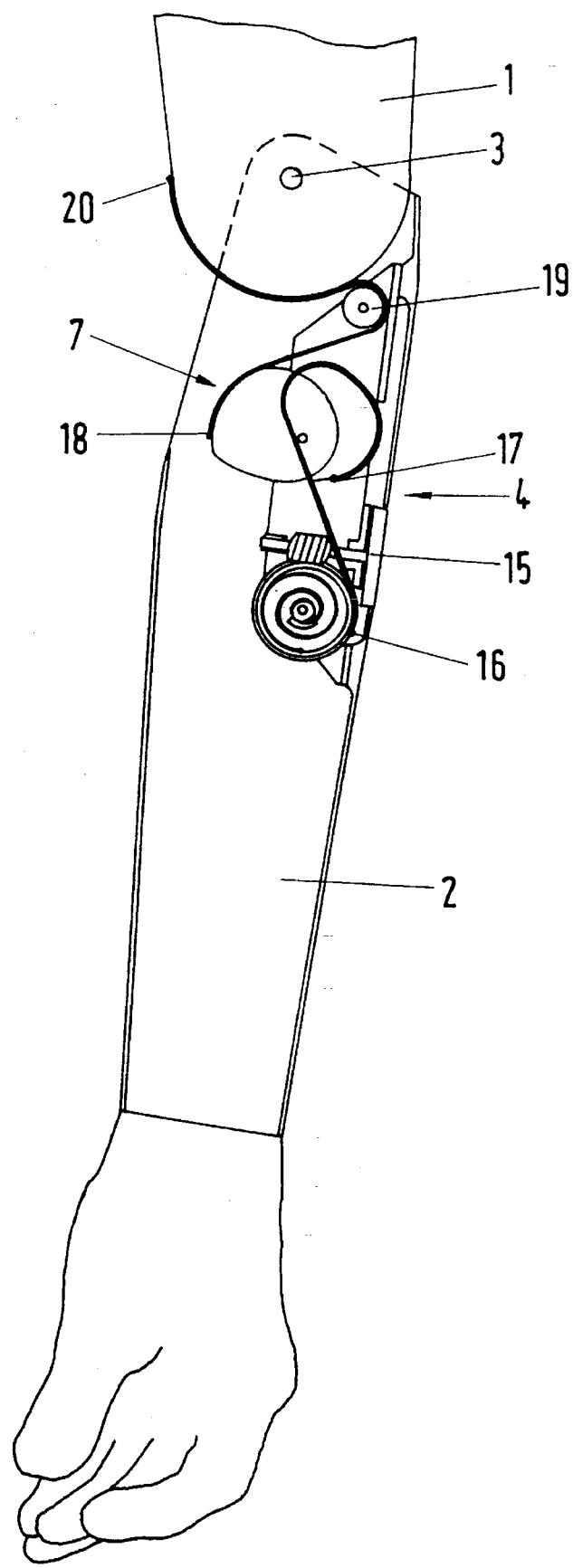
FIG. 1 shows in longitudinal section and partly in side view a complete arm prosthesis with the forearm extended.

The forearm lifter comprises a spring element which directly or indirectly applies a tensile force to the input of a mechanism. The output of the mechanism acts on one end of a tension element while the other end can be fastened at a fixed point on the mating upper arm part. The fixed point together with the elbow axis defines a torque lever on the mating upper arm part. The tensile force is transmitted through the mechanism in such a manner that the curve of the torque acting at the fixed point of the mating upper arm part, plotted against the angle of bend of the mating forearm part, is approximately parabolic. The torque curve has its minimum values in the extended position from approximately 0° to 45°, preferably 5° to 40° and at maximum forearm bending, with its maximum value at approximately 90°.

This is compared to the previously known forearm lifters, which have a maximum torque at the extended position of the arm, and the torque curve falls almost linearly as the forearm is bent to the maximum angle of bend of the forearm.

According to the present invention, the torque curve of the present invention corresponds exactly to the actual requirements for assisting the bending of the forearm. Given correct adaptation of the system, use can then be made of the swinging phase of the upper arm stump for lifting and lowering of the forearm. It is thereby even possible to dispense with a traction cable which would otherwise be necessary for the control of the forearm, so that the amputee can be given greater freedom of movement.

The spring force may also be expediently varied by an electrical adjustment depending on the angle of bend and on the torque curve. In terms of apparatus, it is advantageous for the adjustment of the spring element to be made by means of a first motor controlled by a sensor. In addition or alternative to the electrical adjustment, the spring force may be reinforced by an electrically applied additional torque. The additional torque is preferably supplied by a second motor 25 (FIG. 4) which applies additional torque to the mating upper arm part. The motor is preferably provided in the region of the elbow axis.

It is advantageous for the spring element to be made adjustable in respect of its tensile force; this adjustment is preferably made manually from the outside.

The spring element is preferably a spiral spring, but could also be a tension spring or any element having a similar storage action.

The spring force could in principle be transmitted between the individual stages of the forearm lifter by rigid elements, such as lever arms, or else by combinations of a lever arm, pivot joints, toothings or the like. However, it is preferable for the mechanism of the forearm lifter to be in the form of a cam disk mechanism. The cam disk mechanism preferably has the following configuration.

a) The cam disk mechanism comprises two cam disks, both of which are mounted on a common shaft for rotation with the latter.

b) A force transmission element which transmits force from the spring element to the cam disk mechanism is a flexurally elastic belt or the like, which at one end acts directly or indirectly on the spring element, and the other end is fastened to said first cam disk at a point which defines the mechanism input. The elastic belt substantially embraces or is substantially in contact the first of the two cam disks when the arm prosthesis is extended. Substantially is defined as the elastic belt being in contact with or embracing at least 50% of the first cam disk.

c) The tension element described above is likewise of flexurally elastic construction and is fastened by one end at a point, which point defines the mechanism output, which is located on the second cam disk. The second cam disk is increasingly embraced by or is increasingly in contact with the tension element with increasing bending of the mating forearm part.

In this arrangement it is preferable for the tension element coming from the second cam disk to be guided around a deflection roller and, guided approximately tangentially, to the bottom contour of the mating upper arm part. To prevent a too rapid forward swinging in the event of heavy overcompensation of the arm, it is advantageous for a hydrodynamic damping means to be integrated into the deflection roller.

Further features and advantages of the invention explained more fully with the aid of two exemplary embodiments.

The arm prosthesis shown in FIG. 1 comprises a mating upper arm part 1 and also a mating forearm part 2, which are articulately (swivelly) connected to one another by means of an elbow axis 3. In order to assist the swiveling (articulation) of the mating forearm part 2 to different bending positions, a forearm lifter 4 is provided. The latter has a casing 5, as shown in FIG. 2, which contains or encloses all its components and which is inserted into an appropriate recess in the mating forearm part 2.

Figure 2:
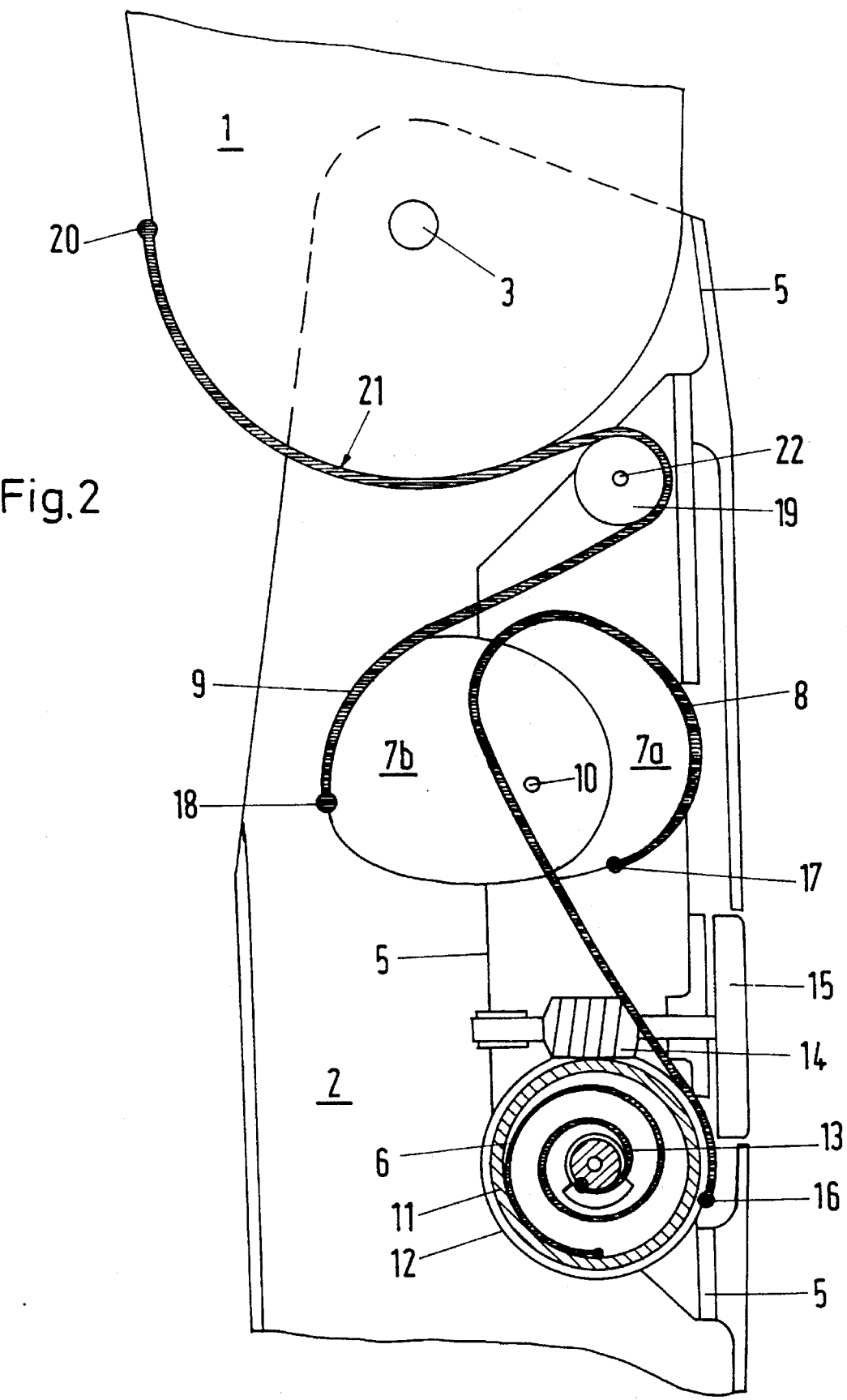
FIG. 2 shows a part of FIG. 1 on a larger scale.

The forearm lifter 4 shown in FIG. 2 essentially comprises a spiral spring 6, a cam disk mechanism 7 (FIG. 1), a force transmission element which transmits the force from the spiral spring 6 to the cam disk mechanism 7 and is in the form of a flexurally elastic belt 8. A tension element 9 kinematically connecting the cam disk mechanism 7 to the mating upper arm part 1 is also provided.

The cam disk mechanism 7 comprises two cam disks 7a and 7b, which are both mounted on a common shaft 10 for rotation with the latter.

The spiral spring 6 is fastened in a spring casing 11 and applies a rotational force to a driven disk 12 which is mounted on an axis 13. The initial stress of the spiral spring 6 can be varied in accordance with the weight to be compensated, which acts on the mating forearm part 2. This variation is made by turning a worm wheel 14. A manually operated rotatable disk 15, a knurled knob or the like, which is accessible from the outside, is provided for operating the worm wheel 14.

The belt 8 is fastened by one end at a fixed point 16 on the driven disk 12. The belt 8 almost completely embraces or is in contact with the external cam contour of the first cam disk 7a. The belt 8 has its other end fastened on the external periphery of said first cam disk 7a by means of a fixed point 17. Fixed point 17 defines the mechanism input of the cam disk mechanism 7.

The tension element 9, which like the belt 8 is flexurally elastic, is fastened at one end to a fixed point 18. The fixed point 18 defines the output mechanism, which output mechanism is on the periphery of the second cam disk 7b. The element 9 is then guided around a deflection roller 19 mounted in the casing 5, and has its other end, which passes out of the casing 5, fastened at a fixed point 20. The fixed point 20 together with the elbow axis 3 defines a torque lever, on the mating upper arm part 1. As shown in FIG. 2 when the mating forearm part 2 is extended, the tension element 9 embraces or is in contact with the external cam contour of the second cam disk 7b only over a short distance. In the region between the deflection roller 19 and the fixed point 20 on the mating upper arm part 1, the tension element 9 lies against the bottom, approximately circular segment-shaped contour 21 of said upper arm part.

Figure 3:
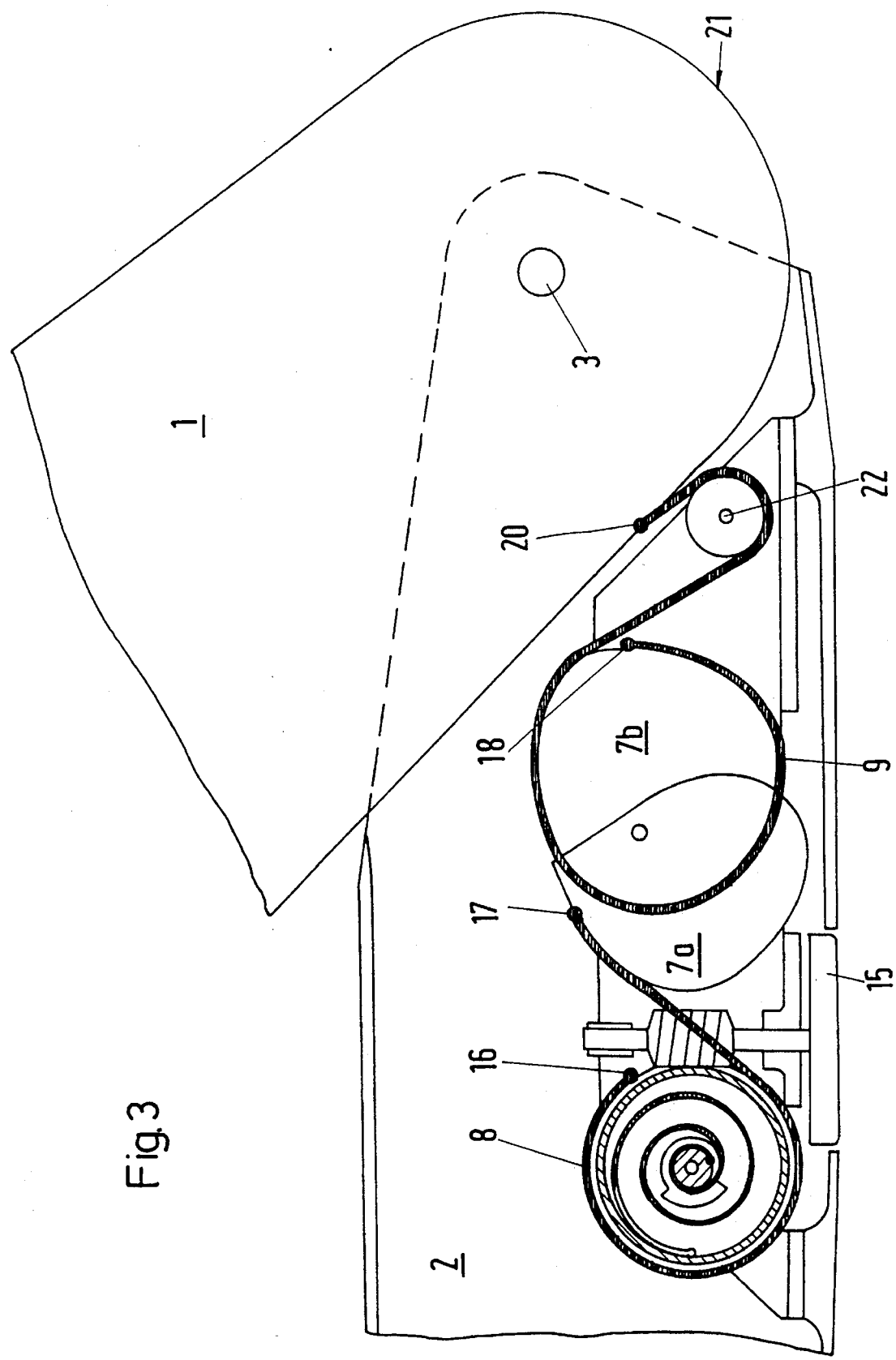
FIG. 3 is a similar view to FIG. 2, but with the forearm sharply bent.

FIG. 3 shows the mating forearm part 2 at its maximum angle of bend. Comparison with FIG. 2 makes it clear that starting from the extended position of the arm, as the angle of bend of the mating forearm part 2 in relation to the mating upper arm part 1 increases, the belt 8 is increasingly wound off the first cam disk 7a and onto the driven disk 12 which is driven by the spiral spring 6. At the same time, the tension element 9 is increasingly detached from the bottom contour 21 of the mating upper arm part 1 and is wound onto the second cam disk 7b. FIG. 3 also shows that the deflection roller 19 is so arranged that the tension element 9 is brought into an approximately tangentially relationship with the contour 21.

Figure 5:
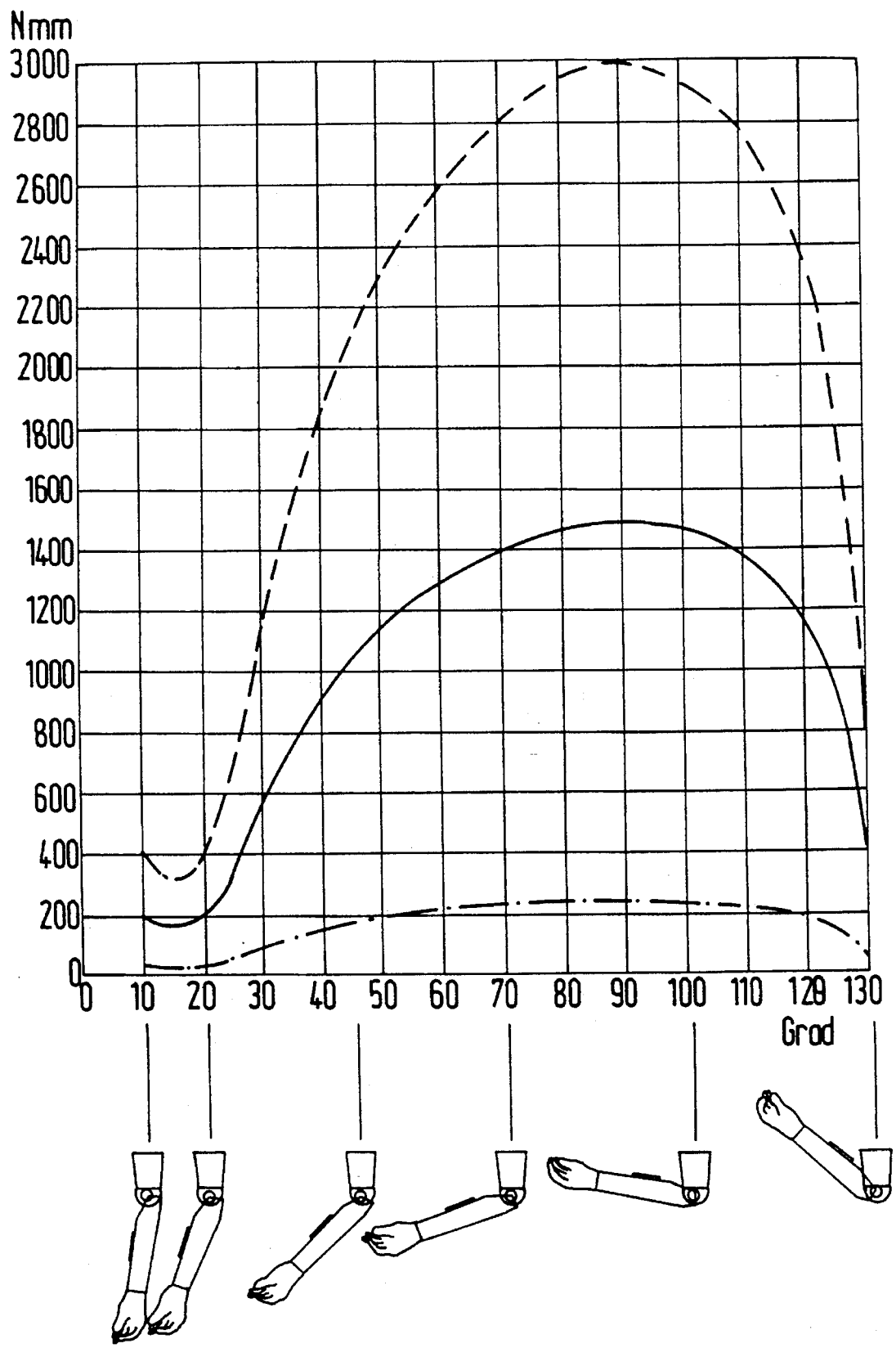
FIG. 5 shows three curves showing torque plotted against the angles of bend of the forearm.

In conjunction with the characteristic of the spring element 6, the cam mechanism 7 is designed so that the curve of the torque applied to the mating upper arm part 1, when plotted against the angle of bend of the mating forearm part 2, is approximately parabolic (see FIG. 5). The curve has its minimum values in the extended position from approximately 5° to 40° and at maximum forearm bending. The curve has its maximum value at approximately 90°. In the embodiments shown in FIGS. 2 and 3 this is achieved by appropriate configuration of the cam paths of the two cam disks 7a, 7b and by their coordination with one another, whereby corresponding compensation of the spring characteristic is also achieved. The broken torque lines plotted against the angle of bend of the mating forearm part 2 in FIG. 5 show the adjustable range of this compensation.

Figure 4:
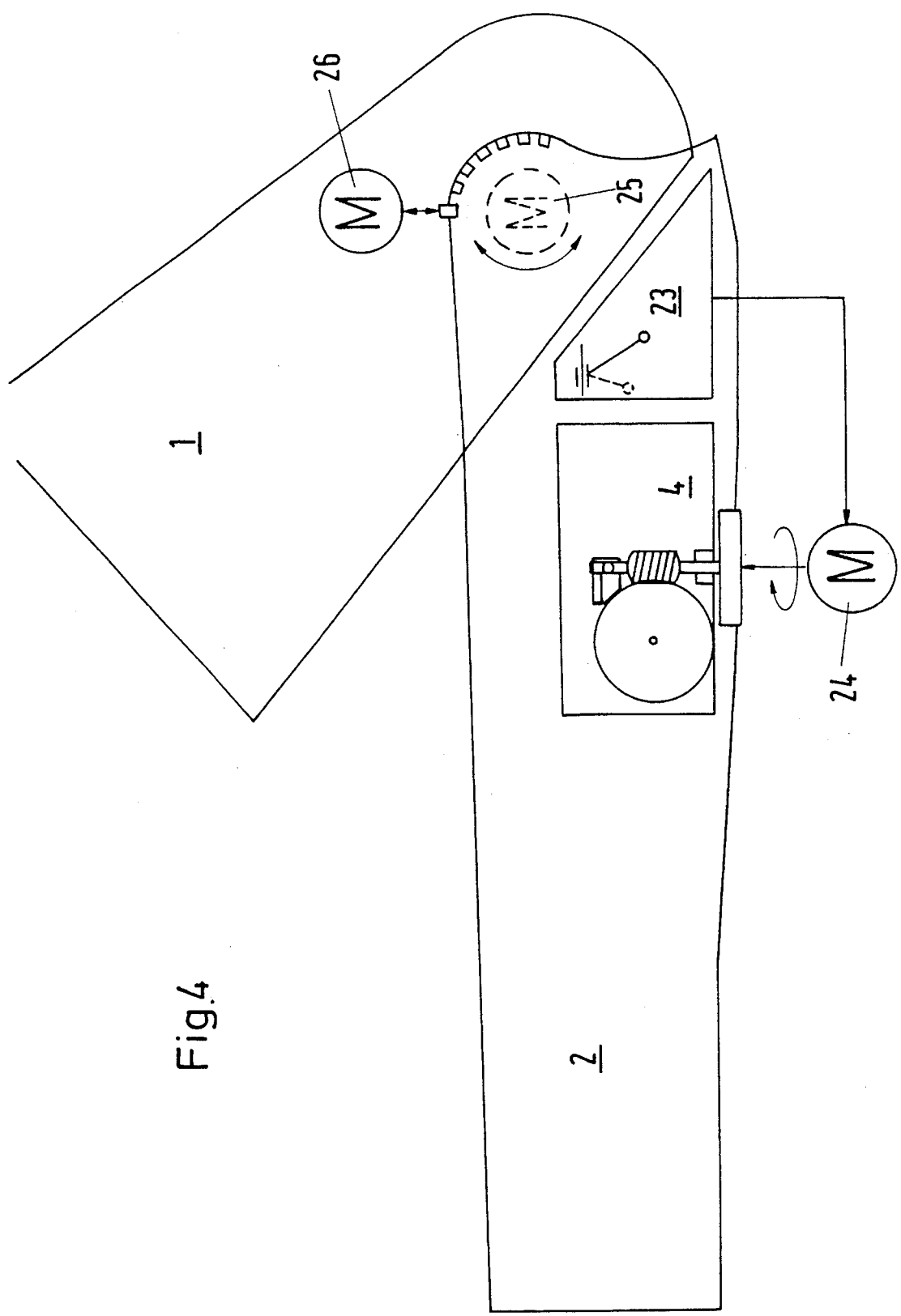
FIG. 4 shows, in a similar view to FIG. 3, an embodiment of the present invention equipped with additional electric drives.

FIG. 4 indicates schematically that the adjustment of the spring element 6 can also be made by means of a first motor 24 controlled by a sensor 23 in dependence on the angle of bend. By means of an electrical adjustment the spring force can thus be varied in dependence on the angle of bend and on the torque curve. Additionally, a second motor 25 applying an additional torque to the mating upper arm part 1 can also be provided in the region of the elbow axis 3. The force of the spring can thus be reinforced electrically. Finally, in FIG. 4 a third motor 26 is also indicated, by means of which the mating forearm part 2 can be electrically secured in a desired bending position.

A comparable kinematic arrangement to that achieved with the two cam disks 7a, 7b could be achieved by appropriate curved configuration of the driven disk 12, the deflection roller 19 and/or the contour 21.

The present invention also comprises a method for applying torque to a mating upper arm part such that the torque curve plotted against the angle of bend of the mating forearm part is approximately parabolic. The torque curve has its minimum values in: (1) the extended position from approximately 0° to 45° preferably 5° to 40°; and (2) at maximum forearm bending. The torque curve has its maximum value at approximately 90°.

Other embodiments of the invention will be apparent to those skilled in the art from consideration of the specification and practice of the invention disclosed herein. It is intended the specification be considered as exemplary only, with the true scope and spirit of the invention being indicated by the following claims.

What is claimed is:

1. A forearm lifter adapted for assisting in the articulation of a mating forearm part of an arm prosthesis with respect to a mating upper arm part about at least one elbow axis, said forearm lifter comprising:

a spring element;

a mechanism having an input and an output, with said spring element directly or indirectly applying a tensile force to the input of said mechanism;

a tension element having one end acted upon by said output of said mechanism, and having another end adapted for fastening at a fixed point on said mating upper arm part; and wherein said fixed point and said elbow axis define a torque lever, such that the force that is transmitted through said mechanism from said spring element is adapted to apply torque to said mating upper arm part in such a manner that the function of the torque acting at the fixed point, plotted against the angle of articulation of said mating forearm part, is approximately parabolic, and said torque having its minimum values in the mating forearm part extended position and at maximum mating forearm part bending, and said torque having its maximum value when said mating upper arm part and said mating forearm part are at approximately 90°.

2. A forearm lifter as claimed in claim 1, wherein said mating forearm part extended position is approximately 5° to 25°.

3. A forearm lifter as claimed in claim 1, wherein said spring element further comprises a spiral spring.

4. A forearm lifter as claimed in claim 1, wherein said spring element is adjustable in order to vary said tensile force applied to said mechanism.

5. An forearm lifter as claimed in claim 3, further comprising a worm wheel for adjusting the initial stress of said spring element.

6. A forearm lifter as claimed in claim 3, further comprising:

a first motor; and a sensor, wherein said first motor and sensor adjust said spring element.

7. A forearm lifter as claimed in claim 1, further comprising:

a driven disk which is driven by a rotational force of said spring element; and a force transmission element fastened to said driven disk, and connected to said mechanism input.

8. A forearm lifter as claimed in claim 1, said forearm lifter further comprises, a force transmission element which acts directly or indirectly on said spring element and is connected to said mechanism input.

9. A forearm lifter as claimed in claim 8, wherein said mechanism comprises a cam disk mechanism.

10. A forearm lifter as claimed in claim 7, wherein:

a) said cam disk mechanism further comprises a first and second cam disk, said first and second cam disk rotatably mounted on a common shaft;

b) said force transmission element further comprises a flexible elastic belt, said belt having one end acting directly or indirectly on said spring element and the other end being fastened at said mechanism input which input is located at a point on said first cam disk, and wherein said elastic belt is in contact with a substantial part of said first cam disk when said forearm is extended; and c) wherein said tension element is of a flexible elastic construction, said elastic tension element having one end located at said mechanism output, which output is located at a point on said second cam disk, and wherein the amount of said elastic tension element in contact with said second disk, is proportional to the amount of articulation of said forearm in the direction of said upper arm.

11. A forearm lifter as claimed in claim 10, said forearm lifter further comprising, a deflection roller, said roller being located such that said elastic tension element coming off of said second disk is guided around said deflection roller such that it is approximately tangential to an approximately circular segment-shaped bottom contour of said mating upper arm part.

12. A forearm lifter as claimed in claim 11, further comprising a hydrodynamic damping means integrated into said deflection roller.

13. A forearm lifter as claimed in claim 11, wherein the elastic tension element, in the region between said deflection roller and said fixed point on said mating upper arm part, lies against the bottom of said approximately circular segment-shaped contour of the mating upper arm portion, when the mating forearm part is extended.

14. A forearm lifter as claimed in claim 4, further comprising a casing for containing or enclosing all the components of said forearm lifter.

15. A forearm lifter as claimed in claim 4, further comprising a second motor located in the region of said elbow axis, for applying an additional torque to said mating upper arm part.

16. A forearm lifter adapted for assisting in the articulation of a mating forearm part of an arm prosthesis with respect to a mating upper arm part about at least one elbow axis, said forearm lifter comprising:

a spring element;

a mechanism having an input and an output, with said spring element directly or indirectly applying a tensile force to the input of said mechanism;

a tension element having one end acted upon by said output of said mechanism, and having another end adapted for fastening at a fixed point on said mating upper arm part;

wherein said fixed point and said elbow axis define a torque lever, such that the force that is transmitted through said mechanism from said spring element is adapted to apply torque to said mating upper arm part in such a manner that the function of the torque acting at the fixed point, plotted against the angle of articulation of said mating forearm part, is approximately parabolic, and said torque having its minimum values in the mating forearm part extended position and at maximum mating forearm part bending, and said torque having its maximum value when said mating upper arm part and said mating forearm part are at approximately 90°, and wherein said forearm lifter is a one-piece integral assembly insertable into a recess of said mating forearm part.

17. A forearm lifter as claimed in claim 16, wherein said mating forearm part extended position is approximately 5° to 25°.

18. A forearm lifter as claimed in claim 16, further comprising a casing for containing or enclosing all the components of said forearm lifter.

19. A forearm lifter as claimed in claim 16, wherein said spring element further comprises a spiral spring.

20. An arm prothesis comprising:

a mating upper arm part;

a mating forearm part; and a forearm lifter for assisting in the articulation of a mating forearm part of an arm prosthesis with respect to a mating upper arm part about at least one elbow axis, wherein said forearm lifter comprises:

a spring element;

a mechanism having an input and an output, with said spring element directly or indirectly applying a tensile force to the input of said mechanism;

a tension element having one end acted upon by said output of said mechanism, and having another end which can be fastened at a fixed point on said mating upper arm part; and wherein said fixed point and said elbow axis define a torque lever, such that the force that is transmitted through said mechanism from said spring element applies torque to said mating upper arm part in such a manner that the function of the torque acting at the fixed point, plotted against the angle of articulation of said mating forearm part, is approximately parabolic, and said torque having its minimum values in the mating forearm part extended position and at maximum mating forearm part bending, and said torque having its maximum value when said mating upper arm part and said mating forearm part are at approximately 90°.

* * * * *